(12) United States Patent  
Sato et al.

(10) Patent No.: US 8,538,772 B2  
(45) Date of Patent: Sep. 17, 2013

(54) HEALTH MANAGEMENT GUIDELINE ADVISING DEVICE

(75) Inventors: Tetsuya Sato, Nishinomiya (JP); Feilang Tseng, Kyoto (JP); Koichi Tanaka, Kyoto (JP)

(73) Assignee: Omron Healthcare Co., Ltd, Kyoto (JP)

( * ) Notice: Subject to any disclaimer, the term of this patent is extended or adjusted under 35 U.S.C. 154(b) by 508 days.

(21) Appl. No.: 12/672,367

(22) PCT Filed: Jul. 15, 2008

(86) PCT No.: PCT/JP2008/062754  
§ 371 (c)(1),  
(2), (4) Date: Feb. 5, 2010

(87) PCT Pub. No.: WO2009/028270  
PCT Pub. Date: Mar. 5, 2009

(65) Prior Publication Data  
US 2011/0106553 A1      May 5, 2011

(30) Foreign Application Priority Data

Aug. 28, 2007   (JP) ................................ 2007-221021

(51) Int. Cl.  
*G06Q 50/00*     (2012.01)  
*G06Q 10/00*     (2012.01)

(52) U.S. Cl.  
USPC ................................................. 705/2; 705/3

(58) Field of Classification Search  
USPC .......................................................... 705/2  
See application file for complete search history.

(56) References Cited

U.S. PATENT DOCUMENTS 5,839,901 A  *  11/1998  Karkanen ..................... 434/127  
6,478,736 B1    11/2002  Mault  
(Continued)

FOREIGN PATENT DOCUMENTS

JP      A-4-204121      7/1992  
JP      A-2002-112976   4/2002  
(Continued)

OTHER PUBLICATIONS

Restraint, weight loss, and variability of body weight. Heatherton, Todd F.;Polivy, Janet;Herman, C. Peter Journal of Abnormal Psychology, vol. 100(1), Feb. 1991, 78-83. doi: 10.1037/0021-843X.100.1.78.*

(Continued)

*Primary Examiner* — Tran Nguyen  
(74) *Attorney, Agent, or Firm* — Oliff and Berridge, PLC

(57) ABSTRACT

A health management guideline advising device includes input means for inputting personal information of a measuring subject; measurement means for measuring weight and body impedance of the measuring subject; estimation means for estimating a body composition distribution of the measuring subject from the inputted personal information and the measurement result by the measurement means; storage means for storing the measurement result by the measurement means and an estimation result by the estimation means with a measurement date and time, prediction means for predicting future weight fluctuation from the stored weight and the body composition distribution; and display means for displaying the predicted future weight fluctuation. Furthermore, target setting means for setting a weight reduction target and determination means for determining whether or not the weight reduction target can be achieved based on the prediction result by the prediction means are preferably arranged.

9 Claims, 10 Drawing Sheets

(56) References Cited

U.S. PATENT DOCUMENTS

| | | | |
|---|---|---|---|
| 6,782,340 B1* | 8/2004 | Komatsu et al. | 702/173 |
| 6,790,178 B1 | 9/2004 | Mault et al. | |
| 2001/0049470 A1 | 12/2001 | Mault et al. | |
| 2002/0062069 A1 | 5/2002 | Mault | |
| 2002/0107433 A1 | 8/2002 | Mault | |
| 2002/0112898 A1 | 8/2002 | Honda et al. | |
| 2003/0065257 A1 | 4/2003 | Mault et al. | |
| 2004/0035611 A1* | 2/2004 | Honda et al. | 177/25.19 |
| 2004/0131227 A1* | 7/2004 | Bravomalo et al. | 382/100 |
| 2004/0131997 A1* | 7/2004 | McGuire et al. | 434/127 |
| 2007/0219059 A1* | 9/2007 | Schwartz et al. | 482/8 |

FOREIGN PATENT DOCUMENTS

| | | |
|---|---|---|
| JP | A-2004-513669 | 5/2004 |
| JP | A-2004-227522 | 8/2004 |
| JP | A-2005-218582 | 8/2005 |
| JP | A-2005-288417 | 10/2005 |
| WO | WO 2007/138822 A1 | 12/2007 |

OTHER PUBLICATIONS

Willett, Guidelines for Healthy Weight, N Engl J Med 1999; 341:427-434 Aug. 5, 1999.*

Goodfellow, From Many Devices That Measure Body Fat, Many Answers, Dec. 24, 1998, The New York Times, Technology.*

"Guidelines for Healthy Weight", WC Willett, the New England Journal of Medicine, Aug. 5, 1999; vol. 341, pp. 427-434.

Office Action dated Sep. 18, 2012 issued in Chinese Patent Application No. 200880104779.4 (with translation).

* cited by examiner

HEALTH MANAGEMENT GUIDELINE ADVISING DEVICE

TECHNICAL FIELD

The present invention relates to a technique of measuring weight and body composition amount of a measuring subject, and advising a guideline useful for health management from the measurement result.

BACKGROUND ART

Many people attempts to lose his/her weight for health and beauty, but there are many problems in losing weight such as the weight cannot be reduced as approach does not last, the weight may increase by a weight rebound after inappropriate approach, and health may be damaged due to unnecessary or excessive weight reduction.

As the conventional technique focusing on the above problems, there is proposed a health state determination device for determining the weight reduction tendency degree from an intraday fluctuation rate of weight (Patent Document 1). According to such a technique, the tendency in change of weight can be recognized by simply looking at the intraday fluctuation, and the motivation to lose weight increases since the user can actually feel the weight reducing in the future before the weight actually reduces.

In order to continue the approach on losing weight, there is disclosed a technique of first setting a weight reduction target (e.g., lose 6 kg in three months), and reducing weight while enjoying by displaying the evaluation on the weight reduction from history data, which is measured daily, with graphs and point scores (Patent Document 2).

The calorie intake is often reduced when losing weight, but a human body has characteristics in that the muscle mass reduces and the basal metabolic rate reduces if the calorie intake is reduced. In the human body, the body is maintained even with few calorie intakes by reducing the basal metabolism.

Weight reduction becomes more difficult when the basal metabolism is reduced. For this reason, the weight steadily reduces at the beginning, but does not steadily reduce from a certain period when reducing weight by cutting the amount of food.

[Patent Document 1] Japanese Unexamined Patent Publication No. 2005-218582
[Patent Document 2] Japanese Unexamined Patent Publication No. 2003-288417

DISCLOSURE OF THE INVENTION

Problems to be Solved by the Invention

The conventional technique does not take into consideration that weight reduction becomes difficult with a reduction in basal metabolic rate.

When evaluating weight reduction as in Patent Document 2, the weight is assumed to reduce at a constant pace every month for the weight reduction target. For instance, in a case where a target of reducing 6 kg in three months is set, evaluation is made that the weight will steadily reduce if weight of 2 kg is lost after one month.

As described above, even if weight of 2 kg is lost in one month, the weight may not steadily reduce in the case where the basal metabolic rate is reducing in the course of weight reduction. In the case where the basal metabolic rate is maintained by exercise, and the like, the weight reduction target may be ultimately achieved even if the weight is not reduced to a large extent at the beginning since the weight reducing pace does not lower thereafter.

Patent Document 1 merely focuses on the daily weight fluctuation, and does not take into consideration the change in basal metabolism.

The tendency of such weight fluctuation is not taken into consideration in the conventional technique, and thus the achievement degree during the weight reduction period cannot be correctly evaluated, and the user may consequently fail in reducing weight.

The present invention has been devised to solve the problems described above, and an object thereof is to provide a technique capable of predicting the fluctuation in weight of a measuring subject at satisfactory accuracy, and advising a guideline useful for health management to the measuring subject based on such a prediction.

To achieve the above object, a health management guideline advising device according to the present invention includes: personal information input means for inputting personal information including at least sex and age of a measuring subject; measurement value input means for inputting weight and body impedance of the measuring subject; estimation means for estimating a body composition amount of the measuring subject from the inputted personal information and the measurement value; prediction means for predicting future weight fluctuation from the weight and the body composition amount; and display means for displaying the predicted future weight fluctuation.

The skeletal muscle mass or the basal metabolic rate is suitably used for the body composition amount for predicting the weight fluctuation.

According to the health management guideline advising device of the present invention, accurate prediction can be made since the future weight fluctuation is predicted in view of the body composition amount. According to the conventional technique, the weight is predicted to reduce at the same pace in the future if weight reduction is performed at a constant pace, whereas a more specific prediction can be made with the health management guideline advising device according to the present invention. For instance, the weight reduction is predicted to be slow when the skeletal muscle mass is reduced even though the weight is steadily reducing. The weight reduction is predicted as not slowing as much when the skeletal muscle mass is not reduced.

Preferably, the health management guideline advising device according to the present invention further includes measurement means for measuring the weight and the body impedance of the measuring subject. Therefore, with the arrangement of the measurement means, the user can know the future weight loss prediction immediately after measuring the weight and the body impedance.

Preferably, the health management guideline advising device further includes storage means for storing a measurement result by the measurement means and an estimation result by the estimation means with a measurement date and time, wherein the prediction means predicts the future weight fluctuation from the stored weight and the body composition amount. A more accurate prediction can be made by predicting the future weight fluctuation based on the history of the past weight and body composition amount.

Preferably, the health management guideline advising device according to the present invention further includes target setting means for setting a weight reduction target value and a weight reduction period and determination means for determining whether or not the weight reduction target is achievable based on the prediction result by the prediction means.

Since the future weight fluctuation can be accurately predicted by the prediction means of the present invention, whether or not the target is achievable can be accurately determined when the weight reduction target is set. Based on such a determination result, the user can judge that further effort needs to be put in if the target cannot be achieved in the current state.

Preferably, the health management guideline advising device according to the present invention further includes target setting determination means for determining whether or not the weight reduction target value or the weight reduction period is appropriate and means for outputting a warning when the target setting determination means determines that the weight reduction target value or the weight reduction period is inappropriate.

The user is prevented from carrying out an unreasonable weight reduction by issuing a warning when rapid weight reduction target that may affect health is set.

In the present invention, when determined that the weight reduction target is not achievable by the determination means, the display means preferably displays an advice to satisfy the weight reduction target. The advice in this case may be to increase amount of exercise to increase the muscle mass (increase basal metabolic rate), reduce number of calories, extend the weight reduction period and the like.

The present invention can be understood as a health management guideline advising device including at least some of the above means. The present invention can also be understood as a health management guideline advice including at least some of the above processes, or a program for implementing such a method. Each means and process can be combined with each other as much as possible to configure the present invention.

According to the present invention, the fluctuation in weight of a measuring subject can be correctly predicted. The guideline useful for health management can be advised to the measuring subject based on such a prediction.

DESCRIPTION OF SYMBOLS

Figure 1:
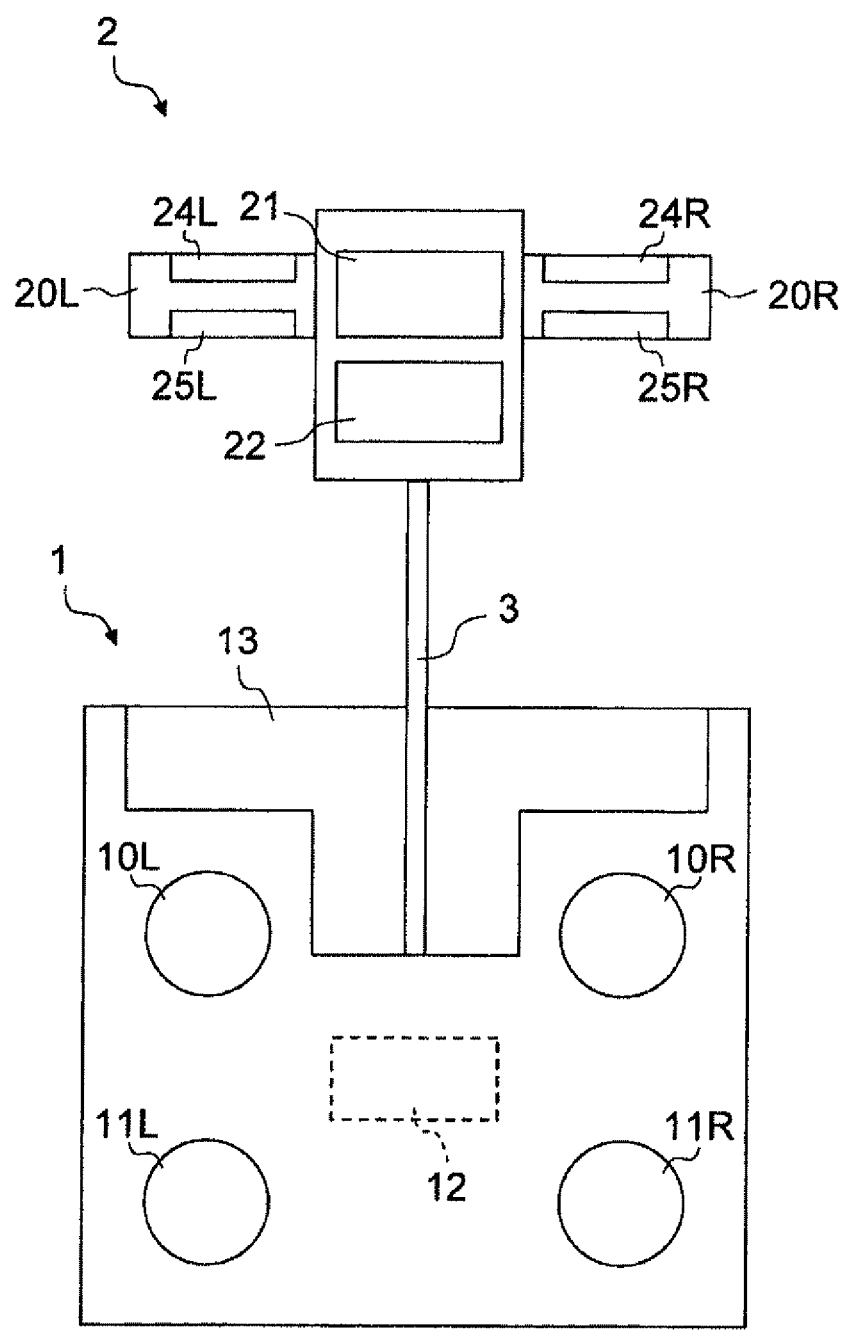
FIG. 1 is a diagram showing a configuration of a health management guideline advising device according to an embodiment.

1 Main body
2 Holder (display operation unit)
3 Cable
10L, 10R Voltage application electrode (for foot)
11L, 11R Voltage detection electrode (for foot)
12 Weight measurement unit
20L, 20R Grip
21 Display unit
22 Operation unit
24L, 24R Voltage application electrode (for hand)
25L, 25R Voltage detection electrode (for hand)
26 Control unit
27 Impedance measurement unit
28 Storage unit
29 Power supply

BEST MODE FOR CARRYING OUT THE INVENTION

Preferred embodiments of the present invention will be illustratively described in detail below with reference to the drawings. It is to be recognized that the dimensions, materials, shapes, relative positions, and the like of the components described in the present embodiment are not intended to limit the scope of the present invention unless a specific description is particularly made.

A preferred embodiment of the present invention will be illustratively described in detail below with reference to the drawings.

In the present embodiment, a configuration example in which the functions of the health management guideline advising device are implemented in a body composition meter is shown.

(Configuration of Body Composition Meter)

FIG. 1 shows an outer appearance of a body composition meter. Here, a weight and body composition meter integrally configured with a weight scale is illustrated.

The body composition meter is broadly configured by a main body 1 and a holder (display operation unit) 2. The main body 1 and the holder 2 are connected with a cable 3 to enable transmission and reception of signals. The main body 1 and the holder 2 may be connected by wireless communication.

When not being used, the holder 2 and the cable 3 are accommodated in a holder accommodation unit 13 of the main body 1.

Four foot electrodes 10L, 10R, 11L, 11R are arranged on the upper surface of the main body 1. The electrodes 10L, 10R are electrodes for applying current to the back of the left and right feet, and the electrodes 11L, 11R are electrodes for detecting voltage from the back of the left and right feet. A weight measurement unit 12 is built in the main body 1.

The holder 2 includes left and right grips 20L, 20R, a display unit 21, an operation unit 22, and the like. The display unit 21 is a portion that displays measurement results and guidance and displays weight fluctuation prediction curve, weight reduction target achievement determination result, and the like, which are to be hereinafter described, and is configured by a liquid crystal display and the like. The operation unit 22 includes 24R for selecting a registered number (user) and setting/checking the weight reduction target, and electrodes 25L, 25R for detecting voltage from the palm of the hand.

Figure 2:
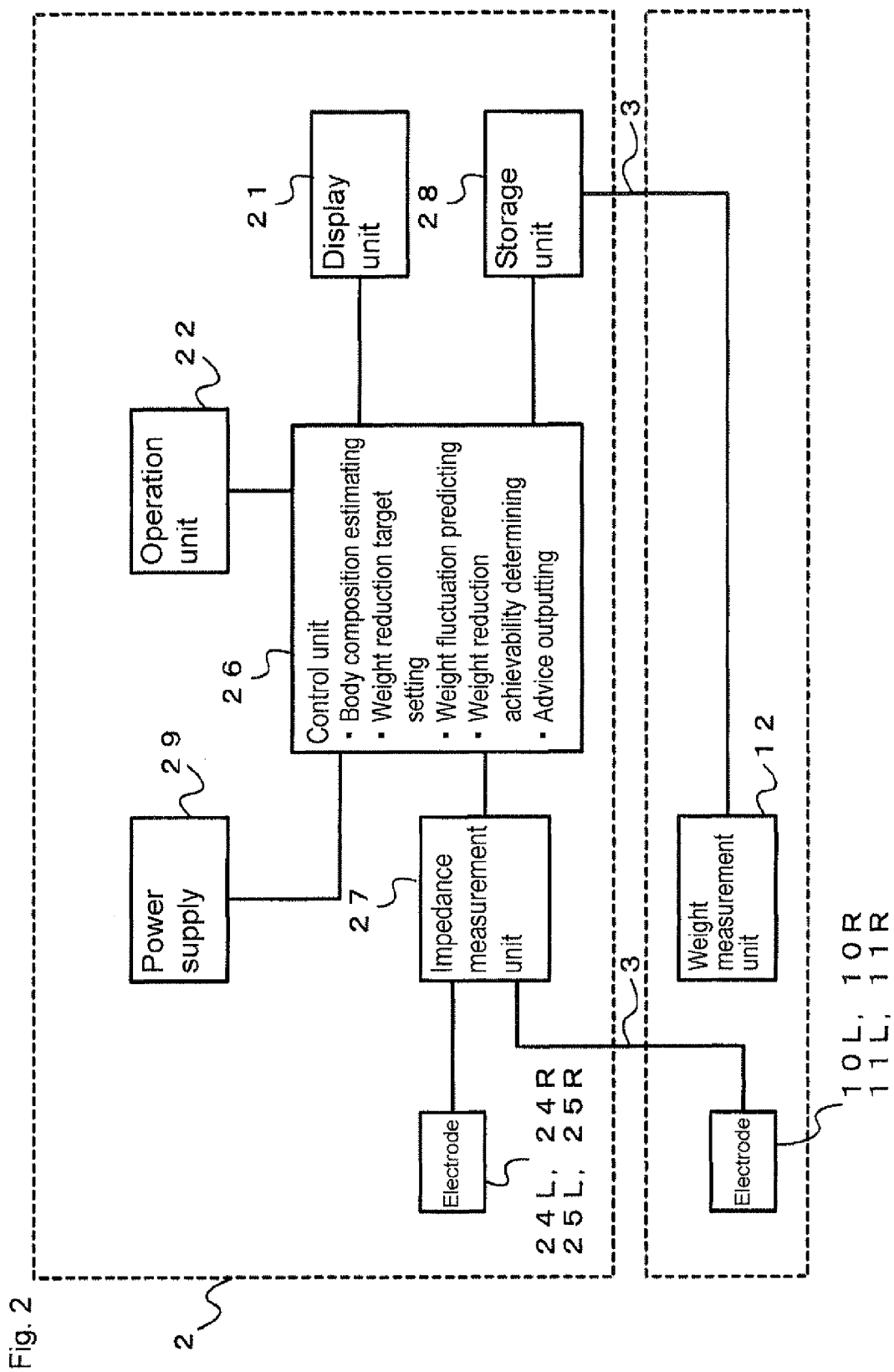
FIG. 2 is a diagram showing function blocks of the health management guideline advising device according to the embodiment.

FIG. 2 is a block diagram showing a configuration of the body composition meter. As shown in FIG. 2, the holder 2 incorporates a control unit 26, an impedance measurement unit 27, a storage unit 28, a power supply 29, and the like.

The control unit 26 is a portion that functions as a body composition estimating function for estimating the body composition, a weight reduction target setting function for setting the weight reduction target, a weight fluctuation predicting function for predicting future weight fluctuation, a weight reduction achievability determining function for determining the achievability of the weight reduction target, an advice outputting function for outputting an advice to achieve the weight reduction target, and the like. Among such functions, the weight reduction target setting function, the weight fluctuation predicting function, the weight reduction achievability determining function, and the advice outputting function are functions of the health management guideline advising device. The control unit 26 is configured by a CPU (Calculation Processing Unit), a memory, and the like, and the above functions are implemented when the CPU executes a program. Some or all functions of the control unit 26 may be configured by a dedicated chip.

The impedance measurement unit 27 is means for measuring the impedance of the body by applying a predetermined current to a living body from the foot electrodes 10L, 10R and the hand electrodes 24L, 24R according to the control of the control unit 26, and detecting the voltage with the foot electrodes 11L, 11R and the hand electrodes 25L, 25R. Specific functions and processes of the control unit 26 and the impedance measurement unit 27 will be described later.

The storage unit 28 is configured by a storage medium such as a non-volatile memory. The storage unit 28 stores the measurement results (measurement values) of the weight and the body composition in time-series by users (by registered numbers). The storage unit 28 also stores body specifying information (sex, age, height) of each user. In the body composition meter of the present embodiment, a plurality of (e.g., four) users can be registered, and the user can be selected by specifying the registered number with the operation unit 22.

(Body Composition Measuring Function)

Figure 3:
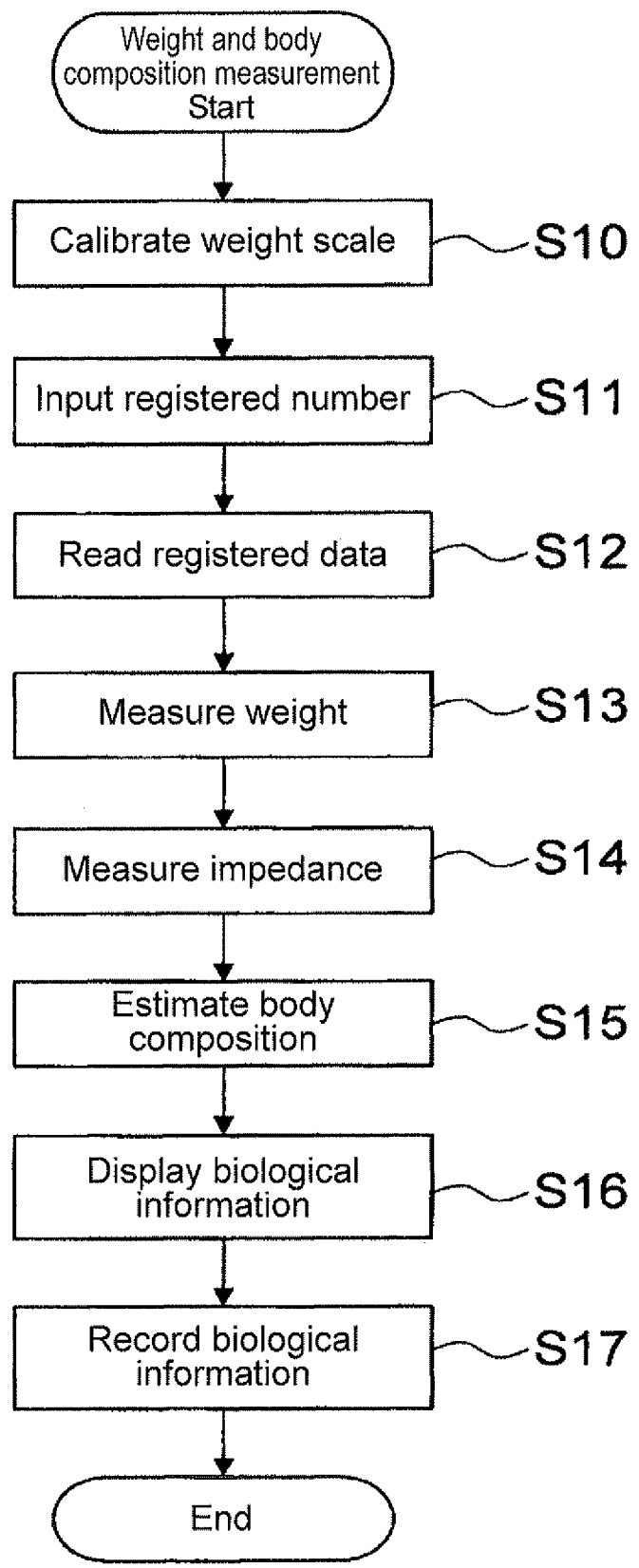
FIG. 3 is a flowchart showing a flow of a weight and body composition measurement process.

The flow of a standard process in measuring the weight and the body composition will be described along the flowchart of FIG. 3.

When the user turns ON the power of the body composition meter, the control unit 26 executes a calibration process of the weight scale (S10). After calibration is finished, the user (registered number) can be selected. When the registered number is specified by the user (S11), the control unit 26 reads the data associated with the relevant registered number from the storage unit 28 (S12).

The user gets on to a predetermined position on the main body 1 and remains still at the measuring posture, and the weight is measured by the weight measurement unit 12 (S13). The in vivo impedance is measured by the impedance measurement unit 27 (S14). Such measurement values are inputted to the control unit 26.

The control unit 26 estimates the body composition based on the measurement values of the weight and the impedance, as well as the body specifying information of the user read from the storage unit 28 (S15). For the body composition, body fat percentage, body fat mass, visceral fat percentage, visceral fat mass, subcutaneous fat percentage, subcutaneous fat mass, muscle percentage, muscle mass and the like can be calculated. Guideline information beneficial to health management and diet such as basal metabolic rate, degree of obesity, body age and the like may be generated based on the calculation results. In the present embodiment, the body fat percentage, the muscle percentage, and the basal metabolic rate are used in the processes described later, and thus the information thereof are calculated. Since a known method can be used for the estimation of the body composition and the calculation of the guideline information, specific description thereof will be omitted.

The control unit 26 displays biological information such as weight, body composition, and guideline information on the display unit 21 (S16). The user can check the measurement result by looking at such display. The control unit 26 stores such biological information in the storage unit 28 along with the measurement date and time information (time stamp) (S17). The values of the biological information are then recorded in time-series.

(Weight Reduction Target Setting Function)

Figure 4:
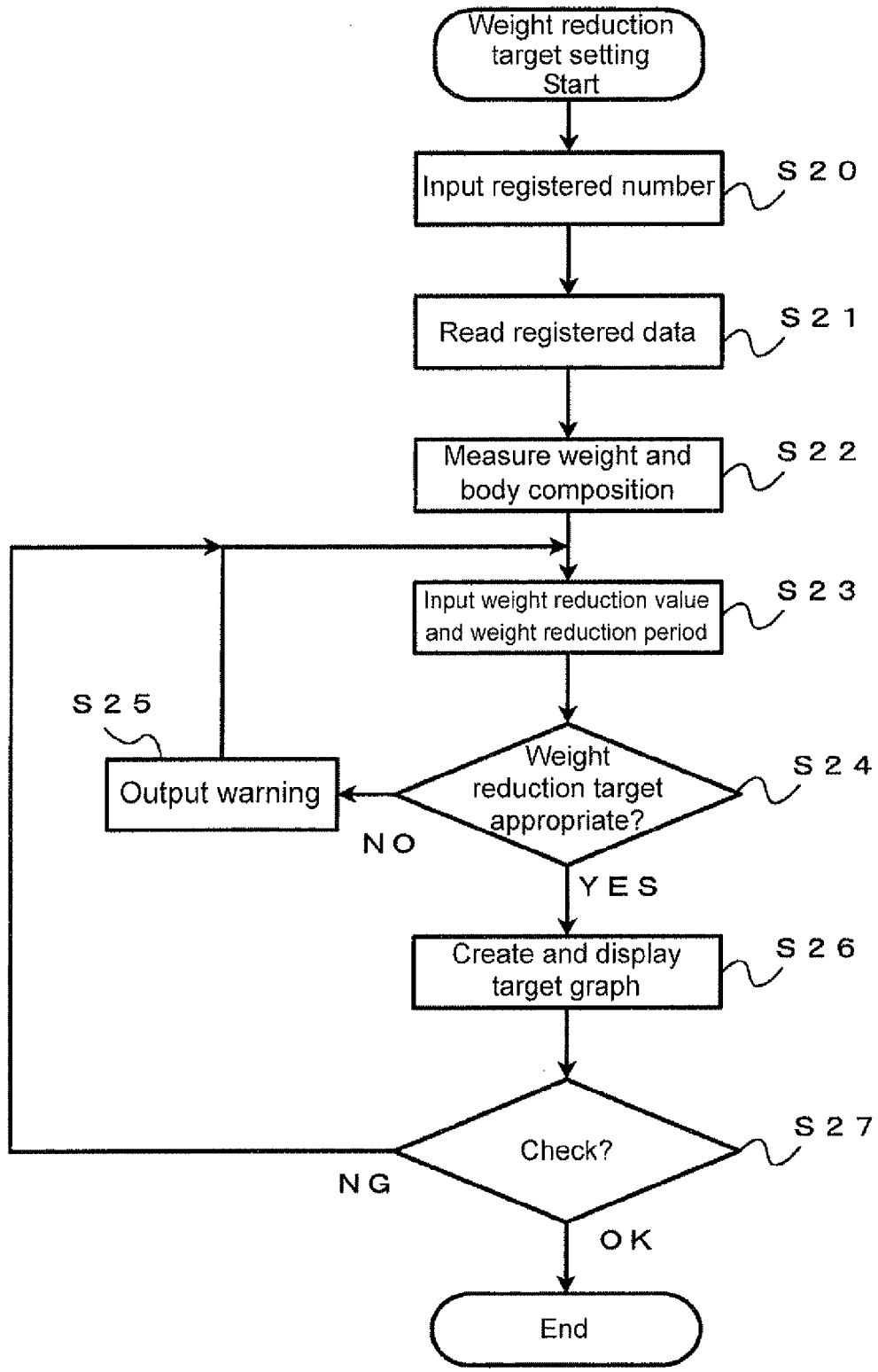
FIG. 4 is a flowchart showing a flow of a weight reduction target setting process.

The flow of the weight reduction target setting process will now be described along the flowchart of FIG. 4. The following process is executed when the user instructs the setting of the weight reduction target using the operation unit 22.

When the registered number is specified by the user (S20), the control unit 26 reads the data associated with the registered number from the storage unit 28 (S21). Here, assume that "sex: female, age: 30, height: 160 cm" are read as personal information.

The current weight value and the body composition distribution are then measured (S22). Here, assume that "weight: 60 kg, body fat percentage: 28.3%, skeletal muscle percentage: 26.9%, basal metabolic rate: 1282 kcal/day" are measured. The measurement result is stored in the storage unit 28.

The weight reduction target value and the weight reduction period are inputted (S23). Here, assume that improvement target is set to reduce weight of 6 kg in three months as in "weight: 54.0 kg, period: three months".

When the weight reduction value and the weight reduction period are set in such a manner, the control unit 26 decides whether or not the weight reduction target is a value that affects health (S24). For instance, the control unit 26 decides that the weight reduction target affects health when a difference (or percentage) between the current value and the target value is greater than a predetermined threshold value, when the weight reduction period is considerably short compared to the weight reduction value, and the like. That is, the setting of the weight reduction target is assumed as inappropriate. When the setting of the weight reduction target is inappropriate (S24—NO), the user outputs a warning, and requests for re-input of the weight reduction target value and the weight reduction period (S25) The reckless target setting can be prevented by the relevant process, and the safety of the weight reduction plan can be guaranteed. The process proceeds to step S26 when the appropriate value is set.

Figure 5A:
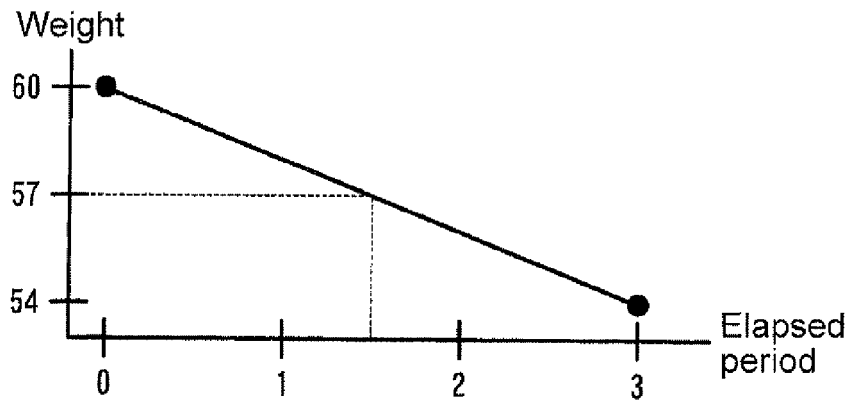
FIG. 5A is a diagram showing a weight fluctuation curve when the weight is assumed to reduce at a constant pace.

In step S26, the control unit 26 creates and displays a target graph showing the fluctuation of the target weight in the weight reduction period based on the set target weight and the weight reduction period. Even when the weight reduction of 6 kg in three months is set, as described above, weight reduction is difficult to continue at a pace of 6 kg/three months, that is, 2 kg/one month, as shown in FIG. 5A. In reality, the weight reducing pace lowers in the second half of the weight reduction period compared to the first half. The percentage in the lowering of the weight reducing pace depends on the change in the basal metabolic rate. The lowering of the weight reducing pace becomes greater the greater the reduction of the basal metabolic rate. The basal metabolic rate greatly depends on the muscle mass.

The control unit 26 creates the target graph in the following manner. First, assume that the muscle mass of the user is maintained in the weight reduction period. In such a case, how to lower the weight reducing pace can be grasped in advance by experiment and the like. For instance, the weight reduction period may be divided into two periods of first half and second half, and the ratio of the weight reducing pace in the second half with respect to the weight reducing pace in the first half can be obtained by experiment.

Figure 5B:
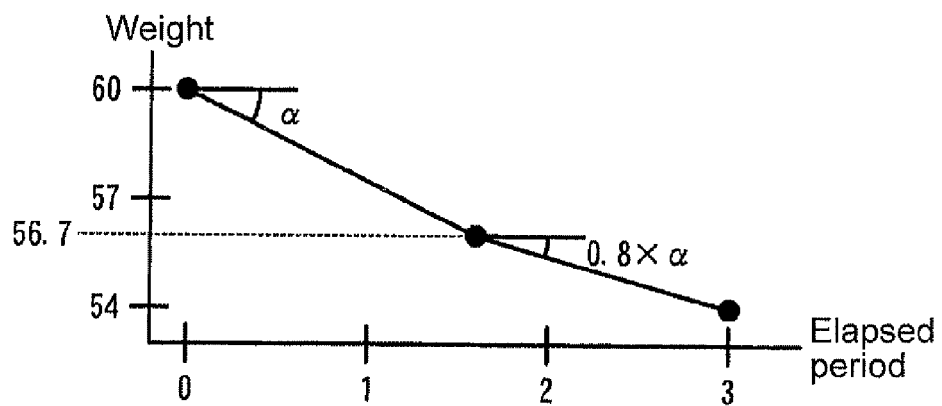
FIG. 5B is a diagram describing a process of calculating a weight fluctuation curve that becomes the weight reduction target, showing a weight fluctuation curve if the weight reducing pace is different for the first half and the second half of the weight reduction period.
Figure 5C:
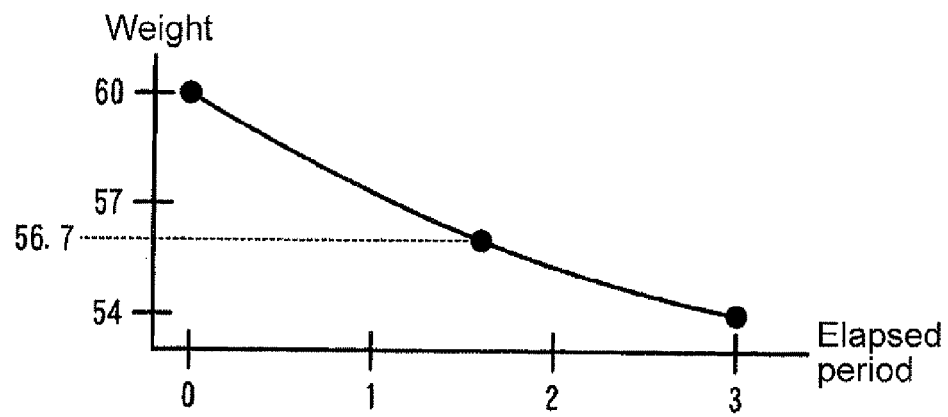
FIG. 5C is a diagram describing a process of calculating a weight fluctuation curve that becomes the weight reduction target, showing a weight fluctuation curve obtained as a quadratic expression passing three points shown in FIG. 5B.

As shown in FIG. 5B, when the weight reducing pace in the second half of the weight reduction period is 0.8 times the first half, weight of 1/(1+0.8)×6=3.3 kg needs to be lost at the intermediate of the weight reduction period if the weight reduction target is 6 kg. A curve connecting three points of an initial value (0 month elapsed, weight: 60 kg), an intermediate value (1.5 months elapsed, weight: 56.7 kg), and a target value (three months elapsed, weight: 54 kg) is obtained. Here, a quadratic expression passing through such three points is obtained. The target graph of the weight fluctuation as shown in FIG. 5C then can be calculated.

The target graph is created with the weight reduction period divided into two and the intermediate target value set, but the weight reduction period may be divided into three or more. In particular, if the weight reduction period is a long period, the period is preferably finely divided. The muscle mass is assumed to be maintained during the weight reduction period in the above description, but the muscle mass may be assumed to reduce a certain extent with the weight reduction period. In such a case as well, how the weight reducing pace becomes can be known in advance by experiment. The slowness of the weight reducing pace in the second half of the period becomes larger the larger the reduction of the muscle mass.

The control unit 26 then displays the created target graph on the display unit 21 and presents the same to the user (S26). Check is requested to the user (S27). When the user is not satisfied (S27-NG), the process returns to the input of the setting of the target value and the weight reduction period (S22). When the user is satisfied (S27-OK), the process is terminated.

(Weight Fluctuation Predicting Process)

Figure 6:
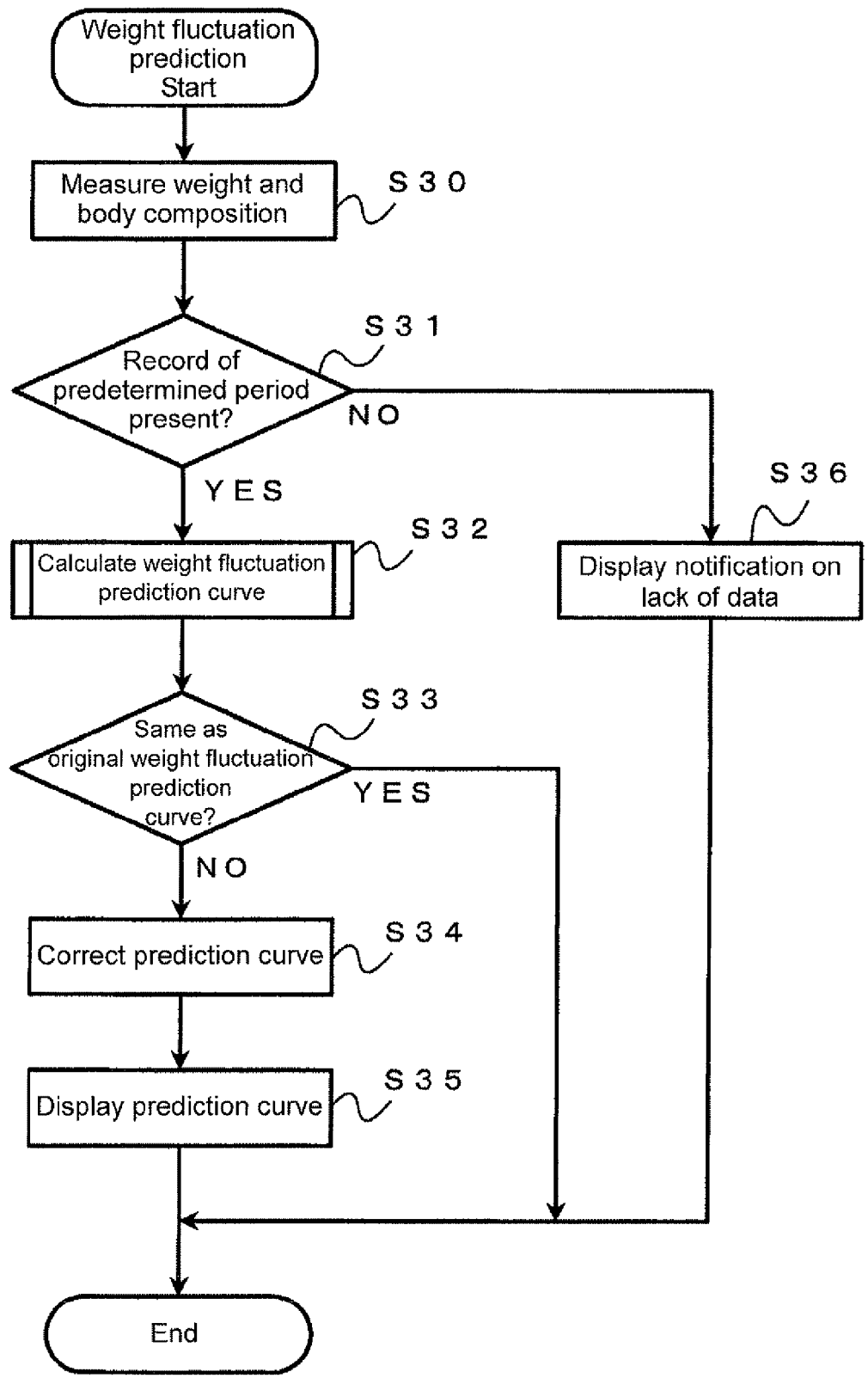
FIG. 6 is a flowchart showing a flow of weight fluctuation predicting process.

The flow of the weight fluctuation predicting process during the weight reduction period will now be described along the flowchart of FIG. 6. First, the weight and the body composition are measured and stored in the storage unit 28 (S30). Whether or not record of a predetermined period is present in the storage unit 28 is determined (S31). The record of a predetermined period is a period in which the data necessary to predict the future weight fluctuation is collected, and whether or not record of four or more days in the recent week is present is determined. When the data stored in the storage unit 28 is few (S31—NO), lack of data is notified (S36), and the process is terminated. If the data is enough, the process proceeds to step S32 and the process continues.

In step S32, the control unit 26 acquires the weight and the body composition from the storage unit 28 and calculates the weight fluctuation prediction curve based thereon. The weight fluctuation prediction curve is a curve indicating how the weight reduces in the future in view of the fluctuation in the weight and the body composition up to the present time. The details on the process of calculating the weight fluctuation prediction curve will be described later.

Whether or not the calculated weight fluctuation prediction curve is the same as the original weight fluctuation prediction curve stored in the storage unit 28 is then determined (S33). When the curves are the same (S33—YES), the process is terminated. When the curves are different (S33—NO), the weight fluctuation prediction curve calculated in step S32 is newly stored in the storage unit 28 (S34), and displayed on the display unit 21 (S35).

[Weight Fluctuation Prediction Curve Calculating Process]

Figure 7:
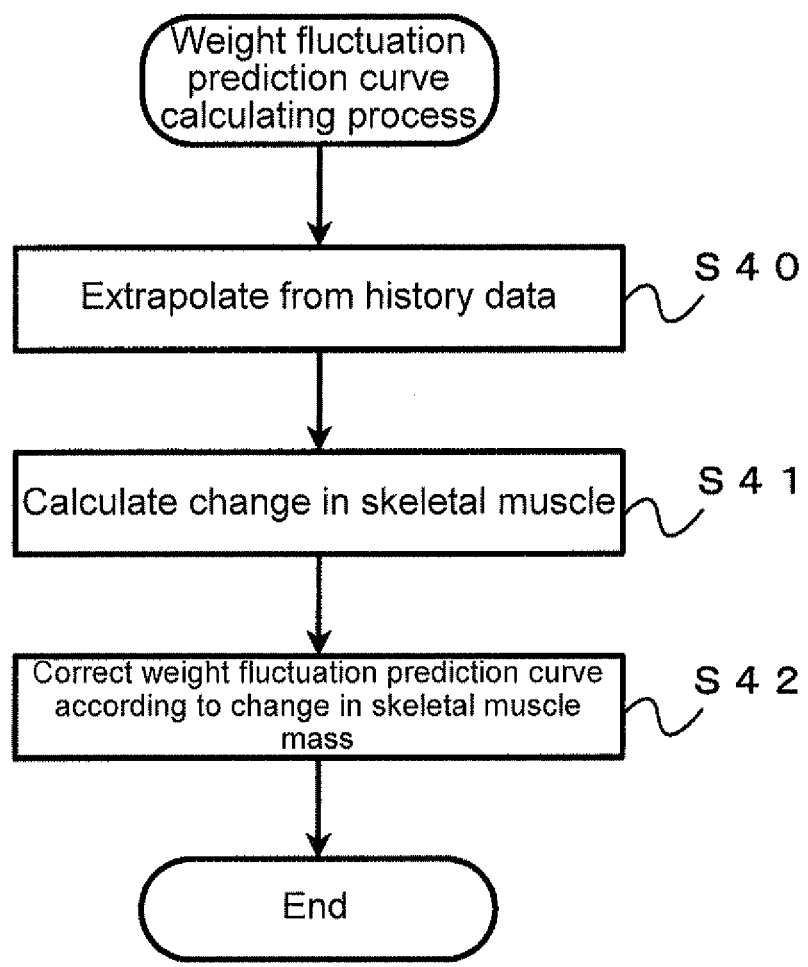
FIG. 7 is a flowchart showing a flow of a process of calculating the weight fluctuation prediction curve.

The details on the process of calculating the weight fluctuation prediction curve in step S32 will now be described with reference to FIGS. 7 and 8.

Figure 8A:
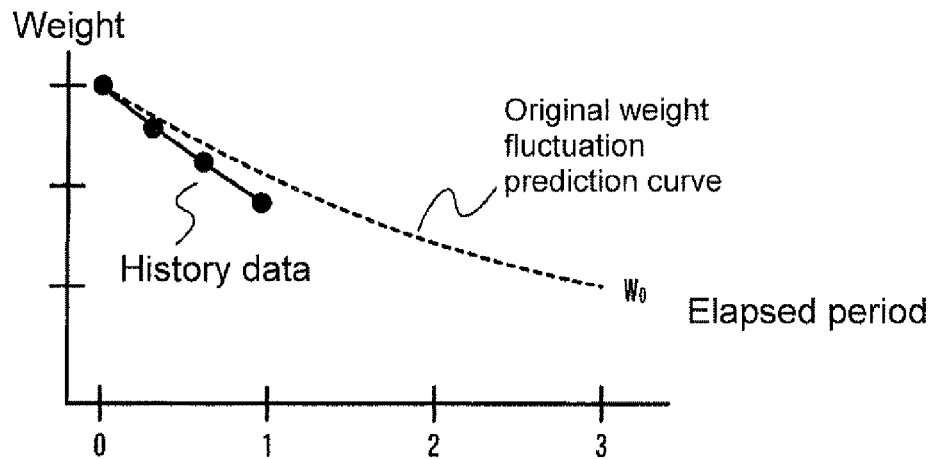
FIG. 8A is a diagram describing a process of calculating the weight fluctuation prediction curve, showing the weight fluctuation prediction curve and the history data of the weight value.
Figure 8B:
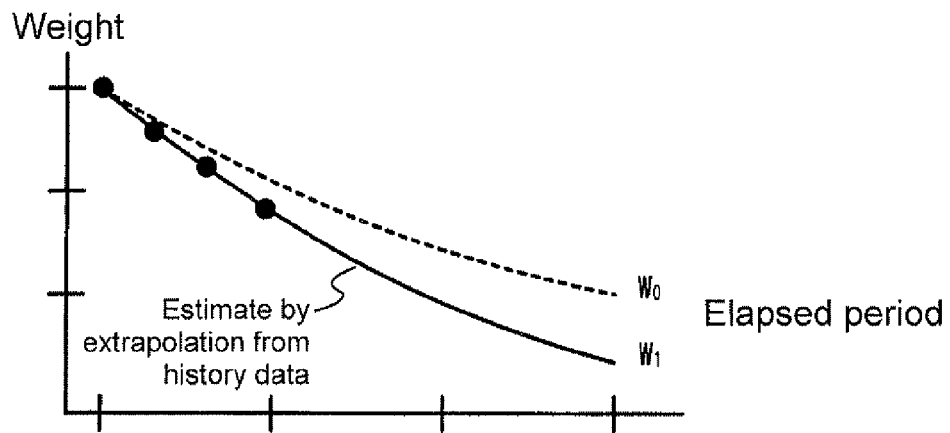
FIG. 8B is a diagram describing a process of calculating the weight fluctuation prediction curve, showing the future weight fluctuation prediction curve obtained by extrapolation from the history data of the weight value.

The control unit 26 estimates the prediction of the future weight fluctuation by extrapolation from the history data of the weight value stored in the storage unit 28 (S40). When the weight reduction is large in the past history data than the original weight fluctuation prediction curve, as shown in FIG. 8A, the estimation is made assuming the weight changes at the pace of the past as shown in FIG. 8B. Specifically, if the weight is reduced 10% more than the original weight fluctuation prediction curve in the past history, correction is made such that the original weight fluctuation prediction curve reduces more by 10% to obtain the prediction curve of FIG. 8B. Thus, in the original prediction curve, the weight after elapse of the weight reduction period predicted as W0 is now predicted as W1.

Here, assumption is made that the weight reduces in the future at the same pace as the past in the calculation of the prediction curve by extrapolation. However, the original weight fluctuation prediction curve is calculated with an assumption on the change in the skeletal muscle mass. For instance, When the original prediction curve is calculated assuming that the skeletal muscle mass does not reduce, reduction may not be made at the relevant pace if the skeletal muscle mass is reduced at the present time. Therefore, the control unit 26 performs correction according to the change in the skeletal muscle mass. Assume that the original weight fluctuation prediction curve is created under the assumption that the skeletal muscle mass does not change.

First, change in the skeletal muscle mass is calculated (S41). The current skeletal muscle mass is obtained by (weight value)×(skeletal muscle percentage). The weight fluctuation prediction curve obtained by extrapolation is corrected according to the change in the skeletal muscle mass (S42). With M0 as the skeletal muscle mass at the start of the weight reduction period and M as the skeletal muscle mass at the current time point, a correction of multiplying a coefficient corresponding to the change (M-M0) in the skeletal muscle mass to the final predicted weight W1 is performed. With the coefficient as e, it can be expressed as e=f(M-M0). Here, f is a function that satisfies $f(x)>1$ when $x<0$, and that satisfies $0<f(x)<1$ when $x>0$. In other words, $e>1$ when the skeletal muscle mass is reducing, and $0<e<a$ when the skeletal muscle mass is increasing. The specific value of the function f can be obtained through experiment and the like.

Figure 8C:
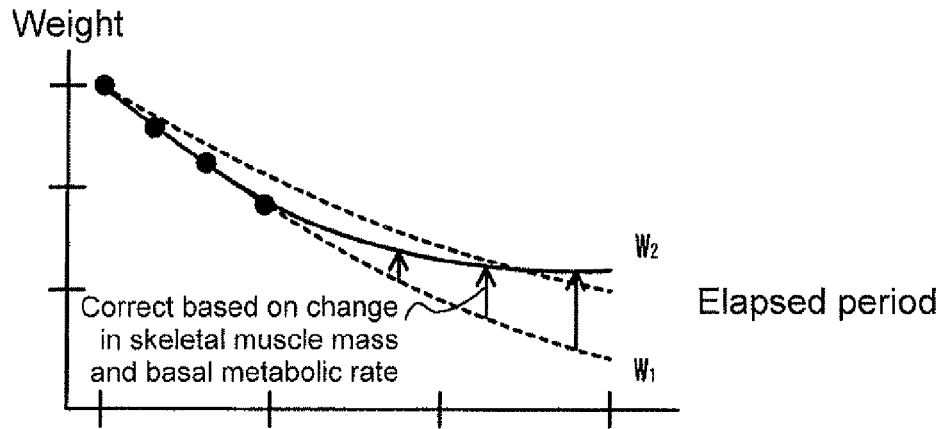
FIG. 8C is a diagram describing a process of calculating the weight fluctuation prediction curve, showing the weight fluctuation prediction curve calculated by correcting the prediction curve by extrapolation of FIG. 8B based on the change in the skeletal muscle mass and the basal metabolic rate.

The final weight W2 of W2=e×W1 is obtained using such a correction coefficient e. As shown in FIG. 8C, the future weight fluctuation prediction curve is calculated by correcting the change curve obtained by extrapolation through the above correction.

If the original weight fluctuation prediction curve is calculated on the premise of reduction of the skeletal muscle mass, correction different from the above is performed. The original weight fluctuation prediction curve is premised on the fluctuation of the skeletal muscle mass, and the correction coefficient corresponding to the fluctuation amount is e0. In this case, the prediction value of the final weight that takes into consideration the change in skeletal muscle mass becomes W2=e/e0×W1.

(Weight Reduction Target Achievement Determining Process)

After calculating the weight fluctuation prediction curve in the above manner, the control unit 26 determines whether or not the weight reduction target set at the beginning is achieved by the predicted weight fluctuation. The determination result is displayed on the display unit 21.

Figure 9:
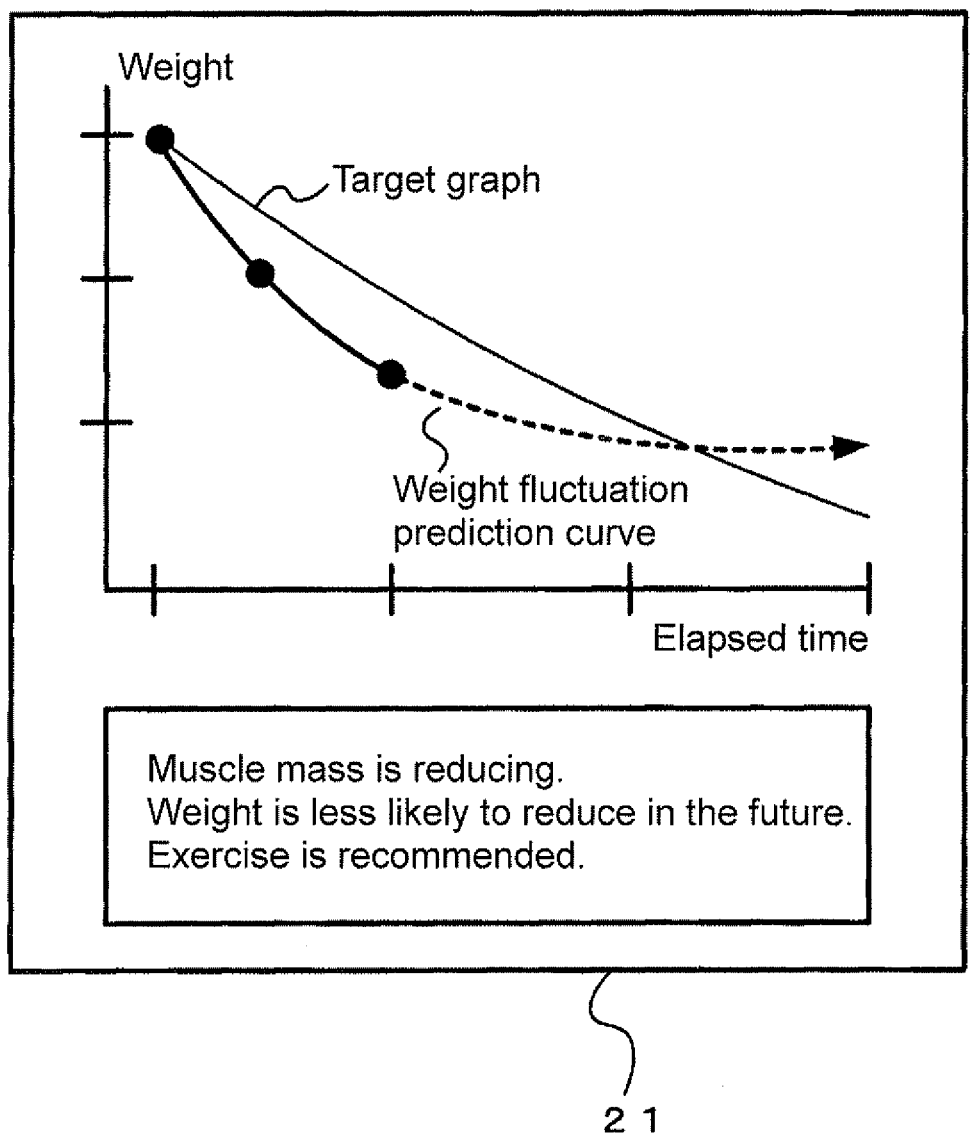
FIG. 9 is a diagram showing a display example of an advice on the weight fluctuation prediction and the weight reduction.

FIG. 9 is a diagram showing a display example of the display unit 21 when the pace of the weight reduction becomes slow and the weight cannot be reduced to the target weight value in the future although the weight reduction is progressing at a pace exceeding the target graph up to the current point. When the skeletal muscle mass is reduced and the basal metabolic rate is lowered, as in the example, display such as "Muscle mass is reducing. Weight is less likely to reduce in the future. Exercise is recommended," is preferably displayed after showing the future weight fluctuation prediction curve, as shown in the figure. Furthermore, history of the skeletal muscle percentage, body fat percentage, basal metabolic rate, and the like are preferably displayed. The user can understand the determination as the user is notified that although the progress seems satisfactory the target cannot be achieved along with reasons thereof.

Figure 10:
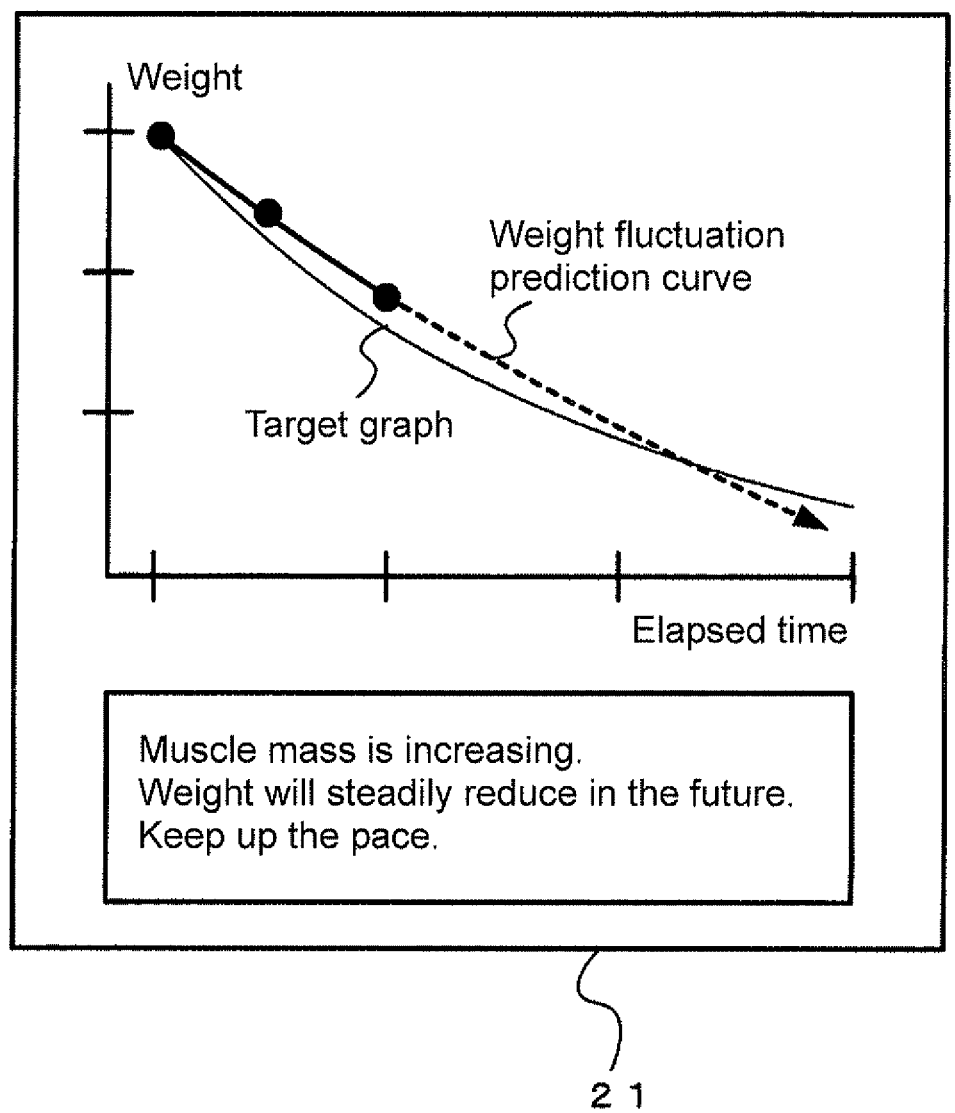
FIG. 10 is a diagram showing a display example of an advice on the weight fluctuation prediction and the weight reduction.

FIG. 10 is a view showing a display example of the display unit 21 when the weight steadily reduces and the weight can be reduced beyond the target in the future although the pace is slightly lower than the target graph up to the current point. When the weight reduction target can be achieved in view of the skeletal muscle mass, the basal metabolic rate, and the like, this is notified to the user so that the user can continue with the approach up to now with relief.

(Variant)

An example in which the health management guideline advising device is incorporated in the body composition meter has been described in the description of the embodiment, but other configurations may be adopted. For instance, the health management guideline advising device may be independent from the body composition meter, so that the weight and the body composition measured in the body composition meter are acquired through communication or a storage medium to predict the future weight fluctuation.

The invention claimed is:

1. A health management guideline advising device comprising:
   a personal information input device configured to input personal information including at least sex and age of a measuring subject;
   a measurement value input device configured to input a weight and a body impedance of the measuring subject;
   an estimation device configured to estimate a muscle mass of the measuring subject from the inputted personal information and the weight and the body impedance;
   a storage device configured to store the weight and the muscle mass;
   a prediction device configured to:
      (i) obtain an amount representing a change of the muscle mass from (a) the muscle mass stored in the storage device and (b) a newly obtained muscle mass, and
      (ii) predict future weight from (a) the weight stored in the storage device, (b) a newly obtained weight, and (c) the amount representing the change of the muscle mass; and
   a display device configured to display the predicted future weight,
   wherein in a condition in which the newly obtained muscle mass is lower than the muscle mass stored in the storage device, the predicted future weight obtained by the prediction device is higher than in a condition in which the newly obtained muscle mass is equal to or higher than the muscle mass stored in the storage device.

2. The health management guideline advising device according to claim 1, further comprising:
   a target setting device configured to set a weight reduction target value and a weight reduction period; and
   a determination device configured to determine whether or not the weight reduction target value is achievable based on a prediction result by the prediction device.

3. The health management guideline advising device according to claim 2, further comprising:
   a target setting determination device configured to determine whether or not the weight reduction target value of the weight reduction period is appropriate; and
   an outputting device configured to output a warning when the target setting determination device determines that the weight reduction target value of the weight reduction period is inappropriate.

4. The health management guideline advising device according to claim 2, wherein when the determination device determines that the weight reduction target value is not achievable, the display device displays advice for satisfying the weight reduction target value.

5. The health management guideline advising device according to claim 1, further comprising a measurement device configured to measure the weight and the body impedance of the measuring subject.

6. The health management guideline advising device according to claim 1, wherein:
   the storage device is configured to store the weight and the muscle mass with a measurement date and time; and
   the prediction device predicts the future weight by performing a correction using the change of the muscle mass such that when the muscle mass is increasing, the future weight is predicted to reduce steadily, and when the muscle mass is decreasing, the future weight is predicted to be less likely to reduce.

7. The health management guideline advising device according to claim 1, further comprising:
   a target setting device configured to set a weight reduction target value and a weight reduction period; and
   a target fluctuation calculation device configured to calculate a target of the weight fluctuation in the weight reduction period such that the weight reducing pace slows down as time advances due to a reduction of the muscle mass.

8. The health management guideline advising device according to claim 1, wherein the muscle mass estimated by the estimation device is a skeletal muscle mass.

9. The health management guideline advising device according to claim 1, wherein the estimation device estimates a basal metabolic rate.

* * * * *